United States Patent
Motafakker-Fard et al.

(10) Patent No.: US 11,172,827 B2
(45) Date of Patent: *Nov. 16, 2021

(54) APPARATUS AND METHOD FOR PROVIDING MESOSCOPIC SPECTROSCOPY CO-REGISTERED WITH OPTICAL FREQUENCY DOMAIN IMAGING

(71) Applicant: The General Hospital Corporation, Boston, MA (US)

(72) Inventors: Ali Motafakker-Fard, Revere, MA (US); Paulino Vacas Jacques, Boston, MA (US); Guillermo Tearney, Cambridge, MA (US); Mireille Rosenberg, Brookline, MA (US)

(73) Assignee: The General Hospital Corporation, Boston, MA (US)

( * ) Notice: Subject to any disclaimer, the term of this patent is extended or adjusted under 35 U.S.C. 154(b) by 447 days.

This patent is subject to a terminal disclaimer.

(21) Appl. No.: 15/944,555

(22) Filed: Apr. 3, 2018

(65) Prior Publication Data
US 2018/0220896 A1 Aug. 9, 2018

Related U.S. Application Data

(63) Continuation of application No. 14/165,827, filed on Jan. 28, 2014, now Pat. No. 9,968,261.
(Continued)

(51) Int. Cl.
*A61B 5/00* (2006.01)
*G01N 21/47* (2006.01)
(Continued)

(52) U.S. Cl.
CPC .............. *A61B 5/0084* (2013.01); *A61B 1/07* (2013.01); *A61B 5/0066* (2013.01);
(Continued)

(58) Field of Classification Search
CPC ... A61B 5/0059; A61B 5/0084; A61B 5/0075; A61B 5/0066; A61B 1/07;
(Continued)

(56) References Cited

U.S. PATENT DOCUMENTS

| 8,953,911 B1* | 2/2015 | Xu | G02B 6/26 |
| | | | 385/12 |
| 2007/0066871 A1* | 3/2007 | Yang | A61B 5/0062 |
| | | | 600/173 |
| 2009/0086213 A1* | 4/2009 | Masuda | G01B 9/02061 |
| | | | 356/479 |

FOREIGN PATENT DOCUMENTS

JP 2010210501 A * 9/2010

OTHER PUBLICATIONS

Translation of Teramura (Year: 2010).*
(Continued)

*Primary Examiner* — Carolyn A Pehlke
(74) *Attorney, Agent, or Firm* — Quarles & Brady LLP

(57) ABSTRACT

An apparatus can be provided according to certain exemplary embodiments. For example, the apparatus can include a waveguiding first arrangement providing at least one electromagnetic radiation. A configuration can be provided that receives and splits the at least one electromagnetic radiation into a first radiation and a second radiation. The apparatus can further include a waveguiding second arrangement which has a first waveguide and a second waveguide, whereas the first waveguide receives the first radiation, and the second waveguide receives the second radiation. The first arrangement, the second arrangement and the configuration can be housed in a probe.

26 Claims, 2 Drawing Sheets

Related U.S. Application Data

(60) Provisional application No. 61/757,444, filed on Jan. 28, 2013, provisional application No. 61/781,857, filed on Mar. 14, 2013.

(51) Int. Cl.
| | |
|---|---|
| *G01N 21/55* | (2014.01) |
| *A61B 1/07* | (2006.01) |
| *G01B 9/02* | (2006.01) |
| *G01J 3/28* | (2006.01) |

(52) U.S. Cl.
CPC ........ *A61B 5/0075* (2013.01); *G01B 9/02091* (2013.01); *G01J 3/2823* (2013.01); *G01N 21/474* (2013.01); *G01N 21/4795* (2013.01); *G01N 21/55* (2013.01); *A61B 2562/0233* (2013.01); *A61B 2576/00* (2013.01); *G01N 2021/4757* (2013.01); *G01N 2021/4761* (2013.01)

(58) Field of Classification Search
CPC . G01B 9/02091; G01J 3/2823; G01N 21/474; G01N 21/4795; G01N 21/55
See application file for complete search history.

(56) References Cited

OTHER PUBLICATIONS

RP Photonics (Fiber Cladding, https://www.rp-photonics.com/fiber_cladding.html, retrieved Jul. 1, 2020).*

* cited by examiner

APPARATUS AND METHOD FOR PROVIDING MESOSCOPIC SPECTROSCOPY CO-REGISTERED WITH OPTICAL FREQUENCY DOMAIN IMAGING

CROSS REFERENCE TO RELATED APPLICATIONS

This application is a continuation of U.S. application Ser. No. 14/165,827 filed Jan. 28, 2014 which relates to and claims priority from U.S. Patent Application Ser. No. 61/757,444 filed Jan. 28, 2013, and U.S. Patent Application Ser. No. 61/781,857 filed Mar. 14, 2013, the entire disclosures of which are incorporated herein by reference.

STATEMENT REGARDING FEDERALLY SPONSORED RESEARCH

This invention was made with Government support under grant number NIH R01 HL093717 awarded by the National Institute of Health. The Government has certain rights therein.

FIELD OF THE DISCLOSURE

The present disclosure relates generally to exemplary methods and apparatus for providing diffuse spectroscopy, and more particularly, to exemplary embodiments of methods and apparatus for providing and/or utilizing diffuse spectroscopy of structures in a catheter. This technique can be performed individually and in conjunction with optical coherence tomography (OCT) and/or frequency domain imaging (OFDI) modalities.

BACKGROUND INFORMATION

A majority of diseases arise within luminal organs such as the coronary arteries and the gastrointestinal tract. Understanding and diagnosis of these diseases can require knowledge of their gross, microscopic, and compositional structure.

An optical imaging catheter has become an important tool to assess and diagnose diseases arising from luminal organs. Since many of the mechanisms involving diseases occur on a microscopic scale, high-resolution imaging and spectroscopy techniques have become relevant. An important technique for high-resolution imaging is optical coherence tomography (OCT) and/or frequency domain imaging (OFDI) modalities, where rotationally scanning catheters can be used for studying the cross-sectional and three-dimensional microstructure of luminal tissues. In addition, absorption spectroscopy in conjunction with rotationally scanning catheters can be used to obtain the compositional content of luminal tissues. However, all of these techniques provide information at a maximum depth of about 1-2 millimeters. Therefore, a method to perform optical imaging of structures located at greater depths would be valuable.

Accordingly, there may be a need to address at least some of the above-described deficiencies.

OBJECTS AND SUMMARY OF EXEMPLARY EMBODIMENTS

In order to address the above-described unmet need and advance to obtain catheter-based diagnosis, it is beneficial to provide an exemplary catheter-based approach/system/apparatus to perform optical absorption spectroscopy at greater depths, and possibly in the diffuse regime (e.g., 2-3 mm deep).

It is one of the objects of the present disclosure to provide exemplary embodiments of catheter-based systems, apparatus and methods to perform a diffuse spectroscopy—, which may include fluorescence spectroscopy, Raman spectroscopy, uv spectroscopy, visible spectroscopy and near infrared spectroscopy (NIRS)—individually and/or in conjunction with OCT and/or OFDI. In accordance with certain exemplary embodiments of the present disclosure, exemplary methods and apparatus can be provided, which facilitate the implementation of the diffuse absorption spectroscopy of structures in, e.g., a catheter.

In order to perform simultaneous compositional and microstructural analysis of luminal tissue, exemplary methods for diffuse spectroscopy (e.g., NIR) combined with optical coherence tomography (OCT) and/or with optical frequency domain imaging (OFDI) can be provided in a catheter. The exemplary method can employ exemplary apparatuses/devices/arrangements according to exemplary embodiments of the present disclosure to illuminate the tissue and collect the scattered light from the tissue. This exemplary technique/method can also utilize source and detectors at different spatial locations, thus facilitating an assessment of the diffuse region. As an example, according to one exemplary embodiment, a maximum source-detector separation of 10 mm can obtain information from approximately 5 mm deep in the tissue.

Thus, an apparatus can be provided according to certain exemplary embodiments of the present disclosure. For example, the apparatus can include a wave guiding first arrangement providing at least one electromagnetic radiation. A configuration can be provided that receives and splits the at least one electromagnetic radiation into a first radiation and a second radiation. The apparatus can further include a waveguiding second arrangement which has a first waveguide and a second waveguide, whereas the first waveguide receives the first radiation, and the second waveguide receives the second radiation. The first arrangement, the second arrangement and the configuration can be housed in a probe.

According to one exemplary embodiment, the first arrangement, the second arrangement and the configuration can be configured to be rotated within the probe. The apparatus can include a drive shaft arrangement which can at least partially enclose the second arrangement. Further, the apparatus can include a lens arrangement which can be provided at an end of the first waveguide and/or the second waveguide. The lens arrangement, upon receipt of the first radiation and/or the second radiation, can illuminate at least one structure. The first and second waveguides can receive third and fourth radiations, respectively, from the structure(s) which can be associated with the respective first and second radiations. The third and fourth radiations received by the first and second waveguides, respectively, can be associated with radiations provided from locations of different portions of the structure(s). The locations can be spatially separated from one another. The spatial separated distance can be at least 1 mm, at least 2 mm, and/or at least 10 mm.

In another exemplary embodiment of the present disclosure, a transparent optical sheath can be provided that can enclose the first arrangement, the second arrangement and the configuration. For example, the first arrangement can include a double-clad fiber and/or a triple-clad fiber. The first arrangement can also have a refractive index profile that can be rotationally symmetric. The first waveguide and/or the second waveguide can be a single mode optical fiber or a multimode optical fiber. The probe can be a catheter and/or an endoscope.

According to yet another exemplary embodiment of the present disclosure, a light modulating arrangement can be configured to modulate an intensity of the electromagnetic radiation(s), thereby modulating an intensity of the third and fourth radiations. The apparatus can also include a processing arrangement can be configured to obtain the intensity information regarding a modulation and a phase of the third and fourth radiations. The processing arrangement can utilize information regarding the modulation and the phase to generate further information regarding the structure(s).

Further features and advantages of the exemplary embodiment of the present, disclosure will become apparent taken in conjunction with the accompanying figures and drawings and upon reading the following detailed description of the exemplary embodiments of the present disclosure, and exemplary claims which follow.

BRIEF DESCRIPTION OF DRAWINGS

Further objects, features and advantages of the present disclosure will become apparent from the following detailed description taken in conjunction with the accompanying figures showing illustrative embodiment of the present disclosure, in which.

Figure 1:
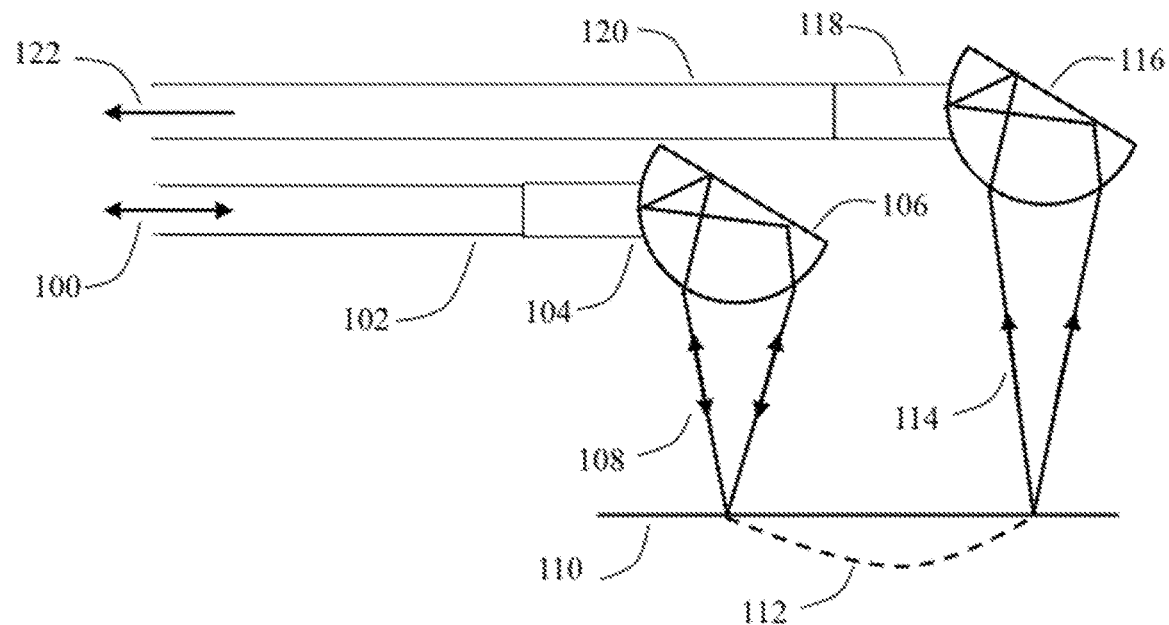
FIG. 1 is a side cross-sectional view of a distal end of an optical coherence tomography-near infrared spectroscopy (OCT-NIRS) optical imaging catheter according to an exemplary embodiment of the present disclosure.

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures, and the exemplary claims which follow.

DETAILED DESCRIPTION OF EXEMPLARY EMBODIMENTS

The exemplary apparatus can also be provided in a probe, a catheter, an eye box, an endoscope, etc. Further, at least one additional fiber can at least be located adjacent to the other fiber(s). In addition, at least one additional fiber can at least be located adjacent to the other fiber(s).

According to an exemplary embodiment of the present disclosure, a device/apparatus/system can be provided which can include an optical coherence tomography (OCT)-diffuse spectroscopy catheter that can illuminate the tissue, and collect signals from the inside of the lumen. Such exemplary device/apparatus/system can generate light source, detect returning light, and/or process signals. An OCT-diffuse spectroscopy rotary junction can rotate and pull back the catheter, and connect the moving catheter to the stationary system. In another exemplary embodiment of the present disclosure, a dual-modality catheter system can be provided for a simultaneous microstructural and compositional deep imaging of arteries in vivo.

For example, an exemplary arrangement/apparatus/device can provide at least one electro-magnetic radiation to an anatomical structure through one or more optical fibers. Such exemplary arrangement can employ the same fiber to perform OCT and/or OFDI imaging, and an adjacent fiber for the diffuse spectroscopy processing. The exemplary arrangement/apparatus/device can also include an apparatus which can be configured to transmit the radiation(s) via OCT and/or OFDI and diffuse spectroscopy fiber(s) to and from the anatomical structure. According to further exemplary embodiments of the present disclosure, other forms of diffuse spectroscopy can be implemented including, e.g., fluorescence spectroscopy, Raman spectroscopy, ultraviolet spectroscopy, visible spectroscopy, etc.

The exemplary arrangement/apparatus/device can be provided in a spectroscopic optical coherence tomography system. Further, a further exemplary system can be provided, which can be configured and/or programmed to obtain information regarding the anatomical structure and deeper structural and compositional information based on the radiation(s) using the diffuse spectroscopy procedures, such as but not limited to, e.g., OCT-NIRS procedure(s).

The exemplary arrangement/apparatus/device can use a fiber coupler inside the OCT-diffuse spectroscopy catheter to facilitate a combination of the returning PCCT and/or OFDI and diffuse spectroscopy light into a double-clad fiber. As described herein, the fiber coupler can be used such that the core signal from the double-clad fiber can be coupled into the core of a single-mode fiber. The returning OCT and/or OFDI light from the single-mode fiber can also be coupled to the core of the double-clad fiber, while the returning diffuse spectroscopy light can be coupled to the inner-cladding of the double-clad fiber.

According to another exemplary embodiment of the present disclosure, the exemplary arrangement/apparatus/device can utilize a fiber coupler inside the OCT-diffuse spectroscopy rotary fiber junction to facilitate a combination of the returning OCT and diffuse spectroscopy light into a double clad fiber. As described herein, e.g., the fiber coupler can be used such that the core signal from the double-clad fiber can be coupled into the core of a single-mode fiber. The returning OCT light from the single-mode fiber can also be coupled to the core of the double-clad fiber, while the returning diffuse spectroscopy light can be coupled to the inner-cladding of the double-clad fiber.

For example, FIG. 1 shows a side cross-sectional view of a distal end of a an OCT-diffuse spectroscopy optical imaging catheter that uses two separate illumination optics (e.g., angle-polished ball lenses) to permit deeper spectroscopy measurements according to an exemplary embodiment of the present disclosure. In this exemplary configuration, an OCT and/or OFDI illumination and detected light/diffuse spectroscopy illumination light 100 can be provided via a first optical fiber 102 and a first spacer 104. One lens 106 (although a plurality of lenses can be used)—which can be a ball lens—can act as the illumination probe for both the diffuse spectroscopy and OCT/OFDI lights 100, while such lens(es) 106 can also collect the returning OCT/OFDI light 100. The illumination probe (e.g., the lens(es) 106) can focus the electromagnetic radiation 108 on a tissue 110. The illumination probe 106 can be used for a collection of the OCT/OFDI light 100, which can then be sent back to an OCT/OFDI processing unit/arrangement/apparatus. A transported light 112 provided through the tissue 110 can be collected through a second collection optics (e.g., lens(es) 116), and sent back to a diffuse spectroscopy processing unit/arrangement/apparatus. For example, a second ball lens 116 can be used to collect a diffuse spectroscopy light 114, provided via a second optical fiber 120 and a second spacer 118, that can be diffused into the tissue 110 using two separate ball lenses. A collected light 122 can be transmitted via the fiber 120 to the diffuse spectroscopy processing unit/arrangement/apparatus.

Figure 2:
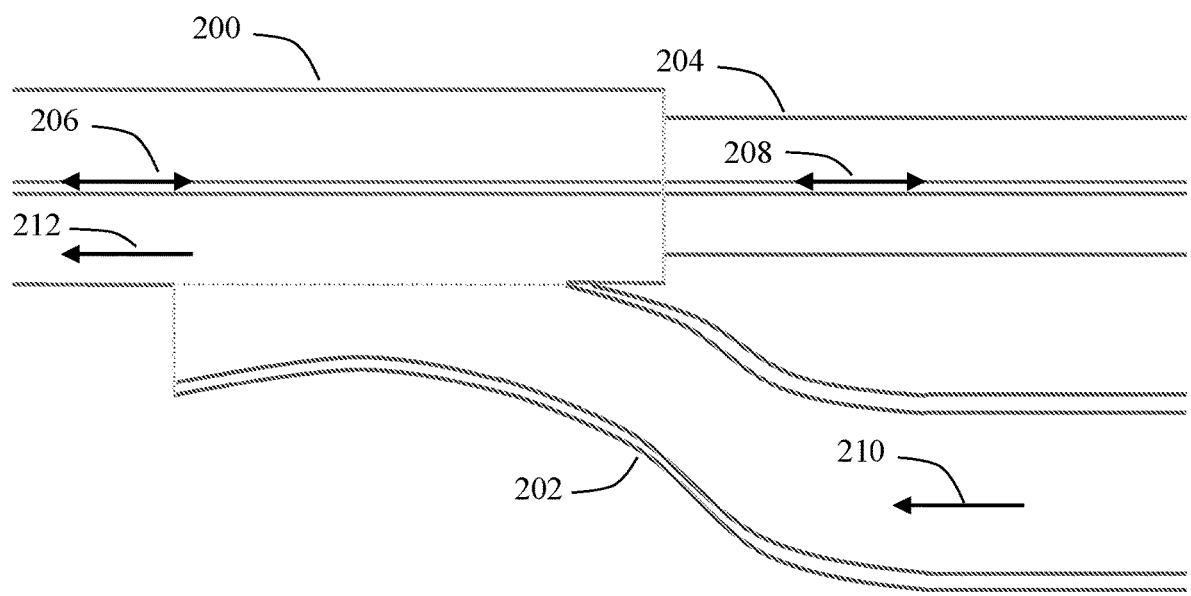
FIG. 2 is a side cross-sectional view of an exemplary implementation of the exemplary OCT-NIRS optical fiber coupler according to the exemplary embodiment of the present disclosure.

FIG. 2 shows a cross-sectional view of a fiber coupler which can be used to implement the exemplary OCT-diffuse spectroscopy system according to an exemplary embodiment of the present disclosure. For example, the exemplary coupler can include a double-clad fiber 200, a multimode fiber 202, and a single-mode fiber 204. In particular, a broadband light or other electro-magnetic radiation can be delivered through a core 206 of the double-clad fiber 200. A signal provided in the core 206 can be coupled to a core 208 of the single-mode fiber 204. The OFDI return light can be transmitted back through the same core 208, while a diffuse spectroscopy return light 210 can be collected via the multimode fiber 202, and can be coupled into an inner cladding 212 of the double-clad fiber 200.

In summary, the exemplary fiber coupler can be placed inside the exemplary catheter of FIG. 1 to facilitate a combination of the returning OCT/OFDI light and/or diffuse spectroscopy light(s) 122 into the double-clad fiber 200. The exemplary fiber coupler can be used such that the returning OCT/OFDI light 100 can be coupled to the core 206 of the double-clad fiber 200, while the returning diffuse spectroscopy light 122 can be coupled to the inner-cladding 212 of the double-clad fiber 200.

Alternatively, e.g., the exemplary fiber coupler can be placed inside a fiber rotary junction to facilitate a combination of the returning OCT light and/or diffuse spectroscopy light(s) 122 into the double-clad fiber 200.

Figure 3:
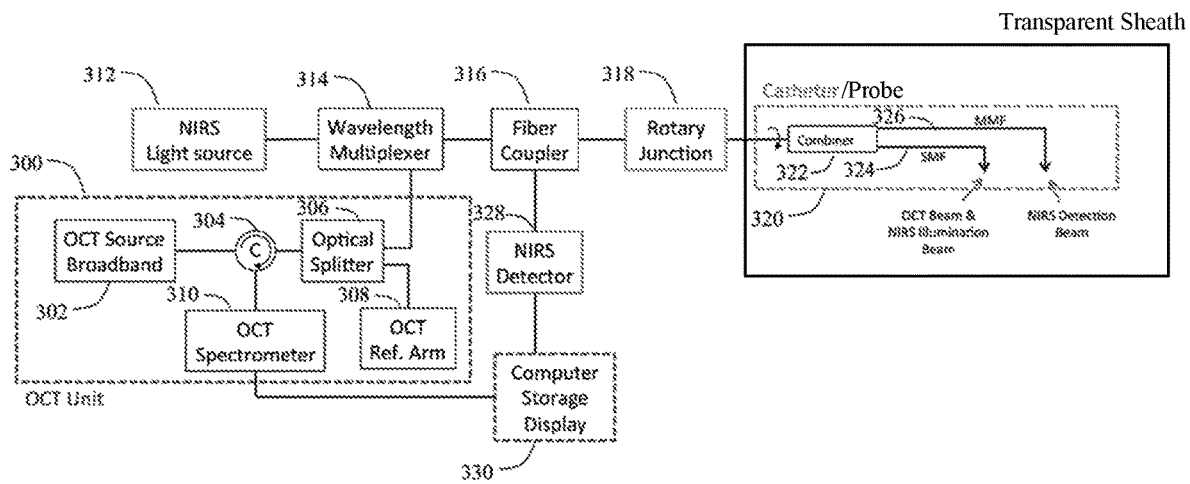
FIG. 3 is a schematic diagram of the OCT-NIRS system according to an exemplary embodiment of the present disclosure.

FIG. 3 shows a schematic block diagram of an exemplary OCT-diffuse spectroscopy system/apparatus according to an exemplary embodiment of the present disclosure. As illustrated in FIG. 3, an SD-OCT apparatus can be provided that can utilize a broadband OCT source 302 and a spectrometer 310. Alternatively or in addition, a swept source can be utilized and photodiode detectors, as can be used for OFDI and/or SS-OCT forms of OCT modalities. In yet another exemplary embodiment of the present disclosure, the form of OCT can be time-domain OCT (TD-OCT), where a broadband source and a moving reference mirror can be utilized in conjunction with photodiode detectors.

Figure 4:
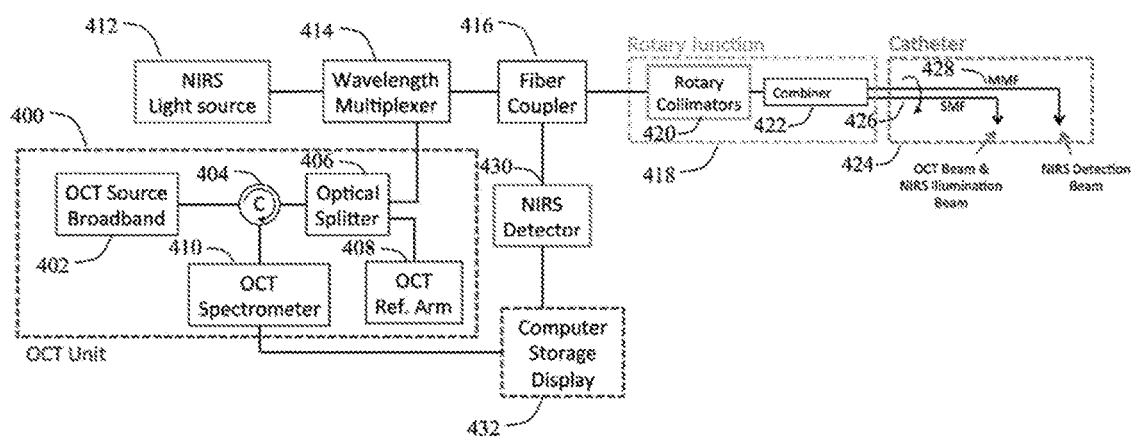
FIG. 4 is another schematic diagram of the OCT-NIRS system (in which a optical fiber combiner arrangement can be placed outside the imaging catheter—inside the rotary fiber junction) according to another exemplary embodiment of the present disclosure.

As shown in FIG. 4, an exemplary OCT-diffuse spectroscopy system can utilize an OCT unit/arrangement/system 300, which for example, can include an OCT source 302, an optical circulator 304, an optical splitter 306, an OCT reference arm 308, and an OCT spectrometer 310. An output of the OCT unit/arrangement/system 300 can be combined with diffuse spectroscopy light source 312 using, e.g., a wavelength multiplexer 314 (or an optical coupler). The combined electromagnetic radiation can enter into the core of a double-clad (or triple-clad) fiber coupler arrangement/device 316. The radiation/light can then propagate through a fiber rotary junction 318. Such propagated radiation/light can then be provided into a double-clad OCT-diffuse spectroscopy catheter 320. Using a combiner arrangement/device 322 (e.g., at least similar to or same as that shown in FIG. 2), the core radiation/light can be transmitted into a single mode fiber (SMF) 324. The OCT and diffuse spectroscopy radiation/lights can illuminate the tissue using an exemplary configuration shown in FIG. 1.

For example, the return OCT/OFDI radiation/light is collected using the SMF 324, while the return diffuse spectroscopy detection light can be collected using a multi-mode fiber (MMF) 326. Most or all return radiation/lights can then be re-combined using the combiner arrangement/device 322 into a double-clad or triple-clad fiber and returned back to the system. The fiber coupler arrangement/device 316 can extract the diffuse spectroscopy radiation/light from the inner cladding, of the double-clad fiber and can transmit it to a diffuse spectroscopy detector 328, while the OCT/OFDI radiation/light from the core of the double-clad fiber can be transmitted back to the OCT unit/arrangement/system 300 for processing. Further, OCT/OFDI and diffuse spectroscopy data can be acquired, processed and displayed using a computer/storage unit/arrangement/system 330.

FIG. 4 shows a schematic block diagram of a further exemplary OCT-diffuse spectroscopy system/apparatus according to another exemplary embodiment of the present disclosure. The exemplary OCT-diffuse spectroscopy system illustrated in FIG. 4 can utilize an OCT unit/arrangement/system 400, which for example, can include an OCT source 402, an optical circulator 404, an optical splitter 406, an OCT reference arm 408, and an OCT spectrometer 410. The output of the OCT unit/arrangement/system 400 can be combined with diffuse spectroscopy light, source arrangement/system 412 using a wavelength multiplexer 414 (or an optical coupler). The combined electromagnetic radiation can enter into a core of a double-clad (or triple-clad) fiber coupler 416. The radiation/light can then propagate through a fiber rotary junction 418. The rotary junction 418 can include static and/or spinning fiber collimators 420 and an optical combiner arrangement/system 422 (e.g., at least similar to or same as those shown in FIG. 2) in which the OCT and diffuse spectroscopy radiation/lights can be transmitted from the core of a double-clad fiber through the core of a single-mode fiber (SMF) 426. The fiber rotary junction 418 can then be interfaced with the exemplary OCT-diffuse spectroscopy catheter 424. The OCT and diffuse spectroscopy radiation/lights can illuminate the tissue using, e.g., an exemplary configuration shown in FIG. 1.

For example, the return OCT radiation/light can be collected using the SMF 426, while the return diffuse spectroscopy detection light is collected using a multi-mode fiber (MMF) 428. Most or all return radiation/lights can then be re-combined using the combiner arrangement/system 422 (e.g., placed in the fiber rotary junction 418) into a double-clad or triple-clad fiber, and returned back to the system. The fiber coupler 416 can extract the diffuse spectroscopy arrangement/system from the inner cladding of the double-clad fiber, and transmit it to diffuse spectroscopy detector 430, white the OCT arrangement/system from the core of the double-clad fiber is transmitted back to the OCT unit/arrangement/system 400 for processing. Finally, OCT and diffuse spectroscopy data are acquired, processed and displayed using a computer/storage unit/arrangement/system 432.

The foregoing merely illustrates the principles of the disclosure. Various modifications and alterations to the described embodiments will be apparent to those skilled in the art in view of the teachings herein. Indeed, the arrangements, systems and methods according to the exemplary embodiments of the present disclosure can be used with and/or implement any OCT system, OFDI system, SD-OCT system, TD-OCT system, or other imaging systems, and for example with those described in International Patent Application PCT/US2004/029148, filed Sep. 8, 2004 which published as International Patent Publication No. WO 2005/047813 on May 26, 2005, U.S. patent application Ser. No. 11/266,779, filed Nov. 2, 2005 which published as U.S. Patent Publication No. 2006/0093276 on May 4, 2006, and U.S. patent application Ser. No. 10/501,276, filed Jul. 9, 2004 which published as U.S. Patent Publication No. 2005/0018201 on Jan. 27, 2005, and U.S. Patent Publication No. 2002/0122246, published on May 9, 2002, the disclosures of which are incorporated by reference herein in their entireties. It will thus be appreciated that those skilled in the art will be able to devise numerous systems, arrangements, and procedures which, although not explicitly shown or described herein, embody the principles of the disclosure and can be thus within the spirit and scope of the disclosure. In addition, all publications and references referred to above can be incorporated herein by reference in their entireties. It should be understood that the exemplary procedures described herein can be stored on any computer accessible medium, including a hard drive, RAM, ROM, removable disks, CD-ROM, memory sticks, etc., and executed by a processing arrangement and/or computing arrangement which can be and/or include a hardware processors, microprocessor, mini, macro, mainframe, etc., including a plurality and/or combination thereof. In addition, certain terms used in the present disclosure, including the specification, drawings and claims thereof, can be used synonymously in certain instances, including, but not limited to, e.g., data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it can be explicitly being incorporated herein in its entirety. All publications referenced above can be incorporated herein by reference in their entireties.

What is claimed is:

1. An apparatus, comprising:
   a first waveguide and a second waveguide rotatably housed in a probe;
   a rotatable combiner optically coupled to the first waveguide and the second waveguide that optically combines light of the first waveguide and the second waveguide into a third waveguide,
   wherein the first waveguide is configured to transmit single-mode light and wherein the second waveguide is configured to transmit multimode light; and
   wherein the third waveguide is optically coupled to the rotatable combiner.

2. The apparatus of claim 1, the third waveguide comprising a core and a cladding,
   wherein the rotatable combiner optically couples the first waveguide to the core of the third waveguide, and
   wherein the rotatable combiner optically couples the second waveguide to the cladding of the third waveguide.

3. The apparatus of claim 1, wherein at least one of the first, second, or third waveguides are optical fibers.

4. The apparatus of claim 3, wherein at least one of the first, second, or third waveguides have a cladding that is configured to transmit light.

5. The apparatus of claim 1, wherein the first waveguide is configured to focus a first electromagnetic radiation at the distal end of the first waveguide, and is configured to emit the first electromagnetic radiation onto a structure and collect a second electromagnetic radiation from the structure.

6. The apparatus of claim 5, wherein the distal end of the first waveguide comprises at least one first lens for focusing the first electromagnetic radiation.

7. The apparatus of claim 5, wherein the second waveguide is configured to focus a third electromagnetic radiation at the distal end of the second waveguide, and is configured to collect the third electromagnetic radiation from the structure.

8. The apparatus of claim 7, wherein the distal end of the second waveguide comprises at least one second lens for focusing the third electromagnetic radiation.

9. The apparatus of claim 8, wherein the at least one first lens is coupled to the distal end of the first waveguide by a first spacer, and wherein the at least one second lens is coupled to the distal end of the second waveguide by a second spacer.

10. The apparatus of claim 1, further comprising a rotary junction, the rotary junction comprising the rotatable combiner optically coupled to a rotatable collimator by the third waveguide.

11. The apparatus of claim 10, wherein the rotatable collimator is optically coupled to an optical coherence tomography (OCT) system.

12. The apparatus of claim 10, wherein the rotatable collimator is optically coupled to a spectral domain optical coherence tomography (SD-OCT) imaging system or an optical frequency domain imaging (OFDI) imaging system.

13. A method, comprising:
    collecting, by a first waveguide, a first electromagnetic radiation;
    collecting, by a second waveguide, a second electromagnetic radiation, wherein the first waveguide is configured to transmit single-mode light and wherein the second waveguide is configured to transmit multimode light; and
    combining, by a rotatable combiner optically coupled to the first waveguide and to the second waveguide, the first electromagnetic radiation and the second electromagnetic radiation into a third waveguide,
       the third waveguide being optically coupled to the rotatable combiner, and
       the first waveguide and the second waveguide being rotatably housed in a probe.

14. The method of claim 13, wherein collecting the first electromagnetic radiation further comprises:
    collecting, by the first waveguide, the first electromagnetic radiation from a first location on a structure, and
    wherein collecting the second electromagnetic radiation further comprises:
       collecting, by the second waveguide, the second electromagnetic radiation from a second location on the structure different from the first location.

15. The method of claim 13, wherein prior to collecting the first electromagnetic radiation, the method comprises:
    emitting, by the first waveguide, a third electromagnetic radiation.

16. The method of claim 15, wherein emitting the third electromagnetic radiation further comprises:
    emitting the third electromagnetic radiation towards a structure, and wherein collecting the first electromagnetic radiation further comprises:
collecting the first electromagnetic radiation from the structure based on emitting the third electromagnetic radiation towards the structure.

17. The method of claim 16, wherein collecting the second electromagnetic radiation further comprises:
collecting the second electromagnetic radiation from the structure based on emitting the third electromagnetic radiation towards the structure.

18. The method of claim 17, further comprising:
performing microstructural imaging of the structure collecting the first electromagnetic radiation from the structure, and
performing spectroscopic imaging of the structure based on collecting the second electromagnetic radiation from the structure.

19. The method of claim 18, wherein performing spectroscopic imaging includes using at least one of a diffuse spectroscopy system, an optical coherence tomography (OCT) system, spectral domain OCT (SD-OCT) system, or an optical frequency domain imaging (OFDI) system,
wherein the at least one of a diffuse spectroscopy system, optical coherence tomography (OCT) system, spectral domain OCT (SD-OCT) system, or optical frequency domain imaging (OFDI) system generates compositional information from the structure.

20. The method of claim 13, wherein the first waveguide is configured to focus a first electromagnetic radiation at a distal end thereof,
wherein the second waveguide is configured to focus a second electromagnetic radiation at a distal end thereof.

21. The method of claim 20, wherein the distal end of the first waveguide comprises at least one lens.

22. The method of claim 20, wherein the distal end of the second waveguide comprises at least one lens.

23. The method of claim 13, wherein the third waveguide comprises a core and a cladding, and
wherein combining the first electromagnetic radiation and the second electromagnetic radiation into the third waveguide further comprises:
combining the first electromagnetic radiation into the core of the third waveguide and the second electromagnetic radiation into the cladding of the third waveguide.

24. The method of claim 23, wherein the rotatable combiner is optically coupled to a rotatable collimator,
wherein the rotatable collimator is coupled to at least one of a diffuse spectroscopy system, an optical coherence tomography (OCT) system, spectral domain OCT (SD-OCT) system, or an optical frequency domain imaging (OFDI) system, and
wherein combining the first electromagnetic radiation and the second electromagnetic radiation into the third waveguide further comprises:
transmitting the first electromagnetic radiation and the second electromagnetic radiation to the at least one of the diffuse spectroscopy system, the optical coherence tomography (OCT) system, the spectral domain OCT (SD-OCT) system, or the optical frequency domain imaging (OFDI) system using the rotatable collimator.

25. The method of claim 13, wherein the probe is at least one of a catheter or an endoscope.

26. An apparatus, comprising:
a first waveguide and a second waveguide rotatably housed in a probe;
a rotatable combiner optically coupled to the first waveguide and the second waveguide that optically combines light of the first waveguide and the second waveguide into a third waveguide;
wherein the third waveguide is optically coupled to the rotatable combiner; and
a rotary junction, the rotary junction comprising the rotatable combiner optically coupled to a rotatable collimator by the third waveguide.

* * * * *

UNITED STATES PATENT AND TRADEMARK OFFICE
CERTIFICATE OF CORRECTION

PATENT NO. : 11,172,827 B2
APPLICATION NO. : 15/944555
DATED : November 16, 2021
INVENTOR(S) : Ali Motafakker-Fard et al.

Page 1 of 1

It is certified that error appears in the above-identified patent and that said Letters Patent is hereby corrected as shown below:

In the Specification

Column 6, Line 57, "white" should be --while--.

Signed and Sealed this
Eighth Day of March, 2022

Drew Hirshfeld
*Performing the Functions and Duties of the*
*Under Secretary of Commerce for Intellectual Property and*
*Director of the United States Patent and Trademark Office*